(12) United States Patent
Lung et al.

(10) Patent No.: US 10,379,123 B2
(45) Date of Patent: Aug. 13, 2019

(54) PEPTIDE, ANTIBODY THEREOF, AND METHOD OF ASSESSING RISK OF ORAL CANCER BY USING PEPTIDE

(71) Applicants: Tunghai University, Taichung (TW); Taichung Veterans General Hospital, Taichung (TW)

(72) Inventors: Feng-Di Lung, Taichung (TW); Ye-song Gu, Taichung (TW); Bor-rung Ou, Taichung (TW); Chi-Sheng Cheng, Taichung (TW); Man-Yee Chan, Taichung (TW)

(73) Assignees: TUNGCHAI UNIVERSITY, Taichung (TW); TAICHUNG VETERANS GENERAL HOSPITAL, Taichung (TW)

( * ) Notice: Subject to any disclaimer, the term of this patent is extended or adjusted under 35 U.S.C. 154(b) by 0 days.

(21) Appl. No.: 15/793,531

(22) Filed: Oct. 25, 2017

(65) Prior Publication Data
US 2018/0113132 A1  Apr. 26, 2018

(30) Foreign Application Priority Data

Oct. 26, 2016 (TW) .............................. 105134605 A
Oct. 6, 2017 (TW) .............................. 106134455 A

(51) Int. Cl.
| | | |
|---|---|---|
| G01N 33/577 | (2006.01) | |
| C07K 14/25 | (2006.01) | |
| G01N 33/574 | (2006.01) | |
| C07K 7/08 | (2006.01) | |
| G01N 33/569 | (2006.01) | |

(52) U.S. Cl.
CPC ......... *G01N 33/57407* (2013.01); *C07K 7/08* (2013.01); *G01N 33/56983* (2013.01); *G01N 33/57488* (2013.01); *G01N 2333/025* (2013.01)

(58) Field of Classification Search
None
See application file for complete search history.

(56) References Cited

U.S. PATENT DOCUMENTS

2008/0200344 A1* 8/2008 Cheng .............. G01N 33/56983
506/9

OTHER PUBLICATIONS

Zhao et al. Expressions of hpv 16-e6 in esophageal carcinoma and its clinical significance. Asian Journal of Medical Sciences, 2015, 6(6): 39-42.*
Wei et al. The distribution of human papillomavirus in tissues from patients with head and neck squamous cell carcinoma. Oncology Reports 28: 1750-1756, 2012.*
Jackson et al. Subcellular localization and quantitation of the human papillomavirus type 16 E6 oncoprotein through immunocytochemistry detection. Virology 435(2013)425-432.*
Stacey et al. Scanning the structure and antigenicity of HPV-16 E6 and E7 oncoproteins using antipeptide antibodies. Oncogene (1994), 9, 635-645.*

* cited by examiner

*Primary Examiner* — Nianxiang Zou
(74) *Attorney, Agent, or Firm* — Muncy, Geissler, Olds & Lowe, P.C.

(57) ABSTRACT

The present application discloses a THLW peptide, an amino acid sequence of which is represented by SEQ ID No. 1. The THLW peptide can be used as a biomarker for diseases, such as oral cancer and cervical cancer, etc., relating to infection of human papilloma virus (HPV), therefore, THLW peptide as an antigen or an anti-THLW peptide antibody prepared can be used to detect the risk of developing cancer for sample providers.

4 Claims, 20 Drawing Sheets

Specification includes a Sequence Listing.

PEPTIDE, ANTIBODY THEREOF, AND METHOD OF ASSESSING RISK OF ORAL CANCER BY USING PEPTIDE

TECHNICAL FIELD

The present application relates to a peptide and use thereof, more particularly to a novel peptide, an antibody thereof, and a method of assessing risk of oral cancer by using the peptide.

BACKGROUND

According to the data from ministry of health and welfare of Taiwan, the number of men who suffer from oral cancer increases year by year, and the oral cancer ranks fifth among the top ten death-causing cancers in Taiwan in 2013. According to statistical data from the world health organization in 2008, more than 260 thousand people worldwide suffer from the oral cancer, and the death of at least 120 thousand people is related to the oral cancer. Taken Taiwan as an example, it is inferred that the reason for the high level of incidence of the oral cancer may be related to habits of chewing betel nut, smoking, and alcoholism and carcinogens contained in diets, of which, chewing betel nut and smoking are main causes for the oral cancer. Specifically, betelin, arecoline, and added flower in the betel nut are carcinogens.

Early symptoms of the oral cancer are not obvious, for example white spots, ulcers, and other early symptoms are often neglected by patients, so that most patients miss the time for treatment in the early stage. With the oral lesion become more serious, obvious symptoms are presented, such as pain, lumps, dysphagia, bleeding, etc., patients begin to seek medical treatment, and however, most patients are diagnosed to be the later stage of the oral cancer when they seek the medical treatment, leading to increase of treatment difficulties. Generally speaking, the patient with 1-2 stage oral cancer has a three-year survival rate of 72% and a five-year survival rate of 60%, while the patient with 3-4 stage oral cancer has a three-year survival rate of 61% and a five-year survival rate of 30%. In addition, at present, the initial clinical examination of oral cancer further requires pathological sections and X-ray examination, in addition to the dependence on the visualization and palpation of doctors, in order to be diagnosed. Although high-risk groups of oral cancer has been actively promoted with screening of the oral cancer, the screening process is invasive type and further requires assistance of specialists, which inhibit the public from actively participating in the screening, let alone that the high-risk groups would periodically participating in the screening, thereby resulting in poor efficacy in prevention or early treatment of the oral cancer.

Thus, it is desired a commercially available kit or method of predicting the risk of oral cancer in vitro that has high sensitivity and easy operation.

SUMMARY OF THE INVENTION

It is a primary objective of the present application to provide a THLW peptide, which has an amino acid sequence represented by SEQ ID No. 1. The peptide can be used as a biomarker for diseases, such as oral cancer, cervical cancer, etc., related to infections of HPV Further, the THLW peptide disclosed by the present application is used as an antigen by those of ordinary skill in the art to prepare a THLW antibody which can specifically bind to an oncogenic protein E6 of the HPV.

It is another objective of the present application to provide a method of detecting the risk of the oral cancer. The method adopts the THLW peptide or/and anti-THLW peptide antibody as detection molecules, and the detection is conducted in a non-invasive manner, so that it can be fast and effectively to detect whether a specimen provider is a high risk group of developing the oral cancer.

It is disclosed a method of detecting risk of developing oral cancer in one embodiment of the present application, the method adopts the THLW peptide to react with a specimen, and when the specimen is responsive to the peptide, it is indicated that the specimen contains a substance that is antigenic to an oncogenic protein E6 of the HPV It is disclosed a method of detecting the risk of developing the oral cancer in another embodiment of the present application, the method comprises the following steps: (a) preparing an anti-THLW antibody, wherein an amino acid of a THLW peptide is represented by SEQ ID No. 1; and (b) allowing the antibody of step a) to react with a specimen; and indicating that the specimen contains human papilloma virus and a specimen provider has a high risk of developing the oral cancer when a variation of an interactive force between the specimen and the antibody is higher than a first preset value, or indicating that the specimen provider has a low risk of developing the oral cancer when the variation of the interactive force between the specimen and the antibody is higher than a second preset value.

Results obtained from the detecting method disclosed by embodiments of the present application can be determined whether the specimen provider is the high-risk group of developing the oral cancer, and can also be used to periodically track the risk of oral cancer or to detect the pre-oral cancer.

Because the HPV-positive oral cancer patient has relatively limited cancerous range, relative sensitivity to chemical treatments, etc., it is known from clinical experience that HPV-positive oral cancer patients have better therapeutic efficacy and prognosis compared to HPV-negative oral cancer patients. Thus, it is still another objective of the present application to provide a method of detecting and assessing a prognosis or therapeutic principle, the method adopts the THLW peptide or/and the anti-THLW peptide antibody as detecting molecules to develop a clinically therapeutic principal to the oral cancer patient or to assess the assistant work for the prognosis, thereby achieving the efficacy of reducing the medical cost and increasing the cure rate.

Further, the first preset value is 100 RU, and the second preset value is 40 RU.

Besides, the THLW peptide and/or the anti-THLW peptide antibody disclosed by the present application can combine detection tools or substrates, for example, bind the peptide or the antibody to biochips or biosensors, to achieve the efficacy of fast determination of the test results.

Preferably, the specimen of the method disclosed in embodiments of the present application is selected from the group consisting of saliva, oral tissue, and blood.

DETAILED DESCRIPTION OF THE EMBODIMENTS

Figure 1:
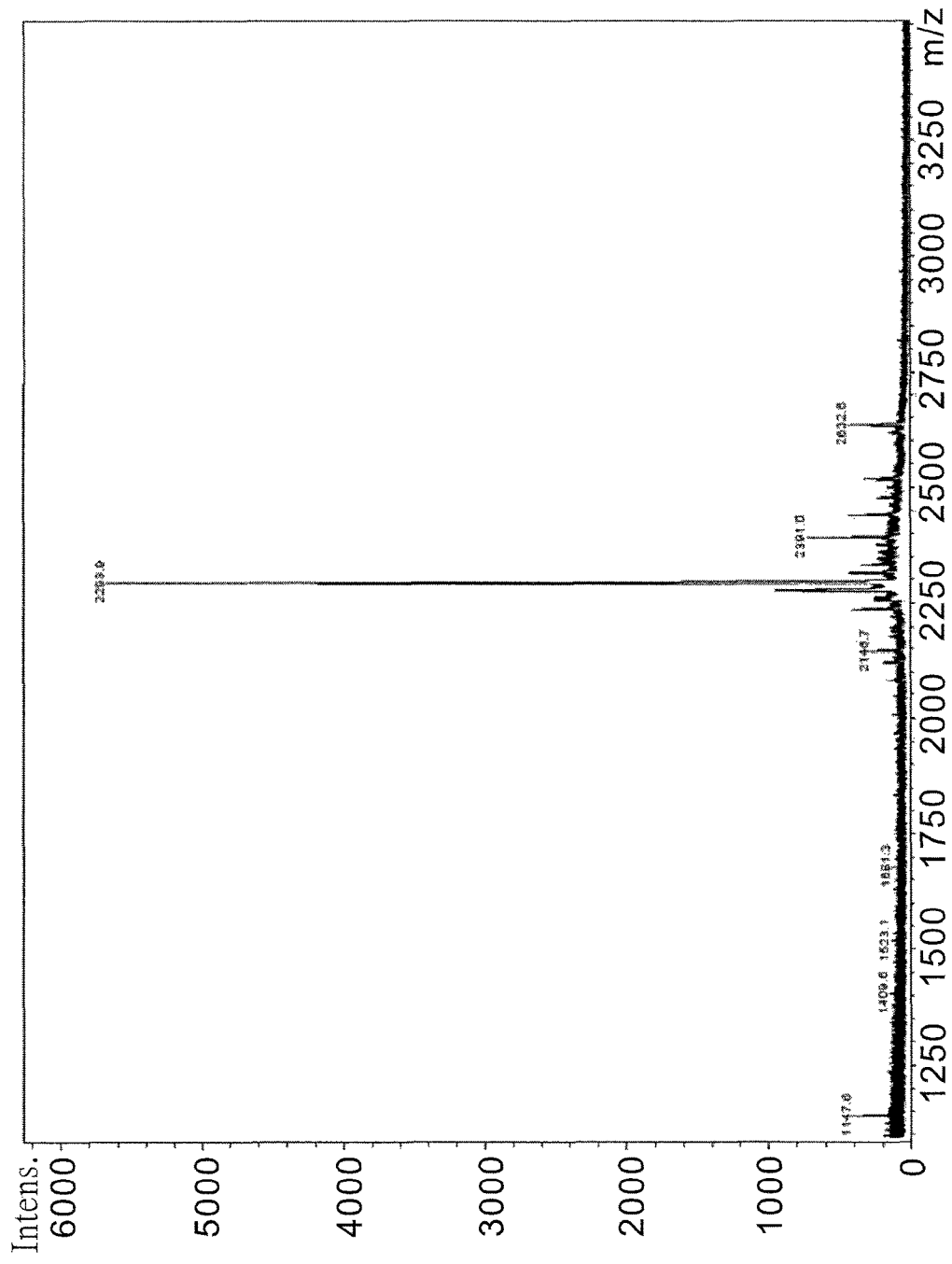
FIG. 1 is a mass spectrogram of a crude product of a THLW peptide.

Unless otherwise defined, meanings of technical and scientific terms used in the description and claim of the present application are the same as those generally understood by those of ordinary skill in the art to which this present application pertains. If there is any contradiction, the contents of the present invention shall prevail.

The present application designs a novel peptide segment, that is, THLW peptide, which has an amino acid sequence represented by SEQ ID No. 1 (EVYDFAFRDL-CIVYRDGNP-amide) and a molecular weight of approximately between 2290 and 2295 Da. By adopting the peptide represented by the SEQ ID No. 1 as an antigen and by adopting the immune operation technics, the antibody can be prepared for use of detecting the oral cancer. The THLW peptide can be prepared by using artificial synthesis or a production platform of recombinant organisms.

The term "artificial synthesis" is a technique known by those of ordinary skill in the art, amino acids are sequentially connected to form a peptide by means of the artificial synthesis, of which, the artificial synthesis includes chemical synthesis and peptide synthesizer. While the artificial synthesis is generally advantageous in that it is convenient to change the primary structure of the peptide, add special amino acid, and modify a terminal of the peptide. In general, the chemical synthesis can be divided into a solid phase peptide synthesis and a liquid phase peptide synthesis, of which, it is required to conduct extraction after each connection of an amino acid in the liquid phase synthesis. However, since the peptide intermediates obtained from the extraction are generally mixtures, it is further required to conduct chromatography purification, thus, the synthesis of peptide based on the liquid phase synthesis must involve complex extraction and chromatography purification in order to obtain highly purified products. The liquid phase synthesis involves performing binding reaction of peptide on solid polymer particles (or polymer supports) in a solvent. In such method, an amino acid which is an N-terminal of a desired peptide is covalently bond to the polymer particles, subsequent amino acids are then sequentially connected by specific binding, until the synthesis of the peptide is completed. Because the polymer particles are insoluble to the solvent, it is only required to conduct washing and filtration operations when the reaction is completed, in order to separate the polymer particles (along with the desired peptide connected on the polymer particles) from a reagent and byproducts. Thus, due that the purification of the intermediates are not necessary, the solid phase peptide synthesis not only possesses relatively good yield but also can greatly shorten the reaction time, besides, the solid phase peptide synthesis is also advantageous in the synthesis of the long-chain peptide, and therefore has been so far the widely used peptide synthesis.

The term of "production platform of recombinant organisms" refers to construct a nuclear acid used to express a specific protein onto an expression vector by biological technique, a resulting recombinant expression vector is thereafter transformed into host cells, such as *Escherichia coli*, yeast, and lactic acid bacteria, etc., so that the recombinant expression vector is able to express the nuclear acid in the host cells and therefore obtain the specific protein.

The term "immune operation technics" refers to antigen-induced immune response to acquire antibodies, of which, the antibodies are polyclonal antibodies or monoclonal antibodies. There are multiple currently known technics for antibody preparation, for instance, the antigen is injected into an organism, such as a mouse, to induce immune response to produce antibodies, after the production of the antibodies are identified, spleen cells and myeloma cells are collected to perform cell fusion, thereafter separated antibodies are acquired. Optionally, the antigens are adopted to infect poultries to make egg yolk thereof contain the antibodies, and thereafter the antibodies are acquired by purification.

The term "biosensor" refers to use immobilized biological recognition molecules, such as antibodies, antigens, carbohydrates, and proteins, etc., to combine with a signal conversion assembly, after the biological recognition molecules react with an analyte, variations in physical quantity, for example quality, optical property, heat quantity, and electric charges, are produced and enable the signal conversion assembly to receive signals of the variations of the biological recognition molecules and then to produce a detectable signal. The biosensor varies according to the energy conversion technique and device, for example, an electrochemical biosensor uses a specific electrode as the signal conversion assembly. While the biosensor using a CM5 chip in this embodiment of the present application is based on SPR, and by converting the variation of refraction coefficient after reaction between the biological recognition molecules and the object to be tested into a variation of resonance angle, the efficacy of the reaction therebetween can be detected.

Hereinbelow, a plurality of examples are enumerated to explain the efficacy of the present application.

It should be firstly explained that because the currently known HPV-16 and HPV-18 are related to oropharyngeal cancer and cervical cancer, of which, HPV-16 enables the host cells to produce protein E6 having an amino acid sequence represented by SEQ ID No. 2 after infecting the host. The protein E6 closes the function of the tumor suppressor protein p53, which causes abnormal proliferation of cells and thereby forms cancer, thus, the protein E6 and its antibody related to the HPV-16 are used as a control group in the following examples.

Example 1 Preparation of THLW Peptide

THLW peptide was prepared using the solid phase peptide synthesis, operation of which was as follows:

A Fomc-AM resin (0.125 mmole, 0.169 mg) was added to a PD-10 tube. 5 mL of dichloromethane was added to expand the resin, the reaction of which lasted for 5 min, and the operation was repeated for twice. Thereafter, 5 mL of dimethylformamide was added to wet the resin, the reaction of which lasted for 5 min, and the operation was repeated for twice.

5 mL of a 30% piperidine/dimethylformamide solution was added and mixed for reaction for 15 min to remove Na-Fmoc protecting group from the resin. Thereafter, 5 mL of dimethylformamide was added and mixed for reacting for 5 min to remove the piperidine/dimethylformamide solution remained in the PD-10 tube by washing. After that, 0.25 mmole amino acid was collected and coupling reacted with (HOBT: 0.25 mmole, 33.775 mg; HBTU: 0.25 mmole, 82.325 mg; and DIEA: 87 µL) for 5 min, a resulting mixture was added to the reaction tube, and mixed and react with the AM resin for 2 hrs. After the reaction, 5 mL of dimethylformamide was added to perform reaction for 5 min, in addition, after each coupling reaction, Ninhydrin test was conducted to identify whether the coupling is successful. The above steps were repeated until all amino acids of the THLW peptide are connected to the resin.

When the sequence of the THLW peptide was completed, 5 mL of the 30% piperidine/dimethylformamide solution was added for reaction, then 5 mL of dimethylformamide solution was added to remove the Fmoc protecting group from the N-terminal of the last amino acid. Finally, the peptide was cleaved from the resin by chemical cleavage, the peptide and the AM resin were cleaved by chemical cleavage, and a lysing reagent (95% TFA in DDW) is utilized to cleave the peptide from the AM resin and to remove the sidechain protective group by cutting. After filtration under reduced pressure and centrifugation were conducted, a crude product of peptide was acquired.

Equal volumes of a predetermined substrate and the crude product of peptide were mixed to form cocrystallization. Thereafter, molecular weight thereof was analyzed, results of which were shown in FIG. 1. The crude product of the THLW peptide contained the target product, i. e., the THLW peptide (having a molecular weight of 2293.9 Da), and the amino acid sequence thereof was represented by SEQ ID No. 1.

Example 2 Purification of Crude Product of Peptide

The crude product of the peptide acquired from Example 1 was analyzed by reversed phase high performance liquid chromatography (RP-HPLC), during which, a chromatography column adopted a C18 column having a pore size of 10 µm, a detection wavelength was 225 nm, and a constant flow rate was 4 mL/min, and a mobile phase solvent was composed as follows: a solvent A: 4 L D. D. water+0.05 trifluoroacetic acid (TFA), and a solvent B: 4 L Acetonitrile+ 0.05 trifluoroacetic acid (TFA) which was added with a trace of TFA; and a content ratio of the solvent A to the solvent B satisfied that the solvent A and the solvent B were rinsed within a ratio range of between 90:10 and 10:90, then the weight ratio of 10:90 was maintained for 7 min, and the weight ratio of 90:10 was maintained for 10 min. Results detected by computer were shown in FIG. 2.

Figure 2:
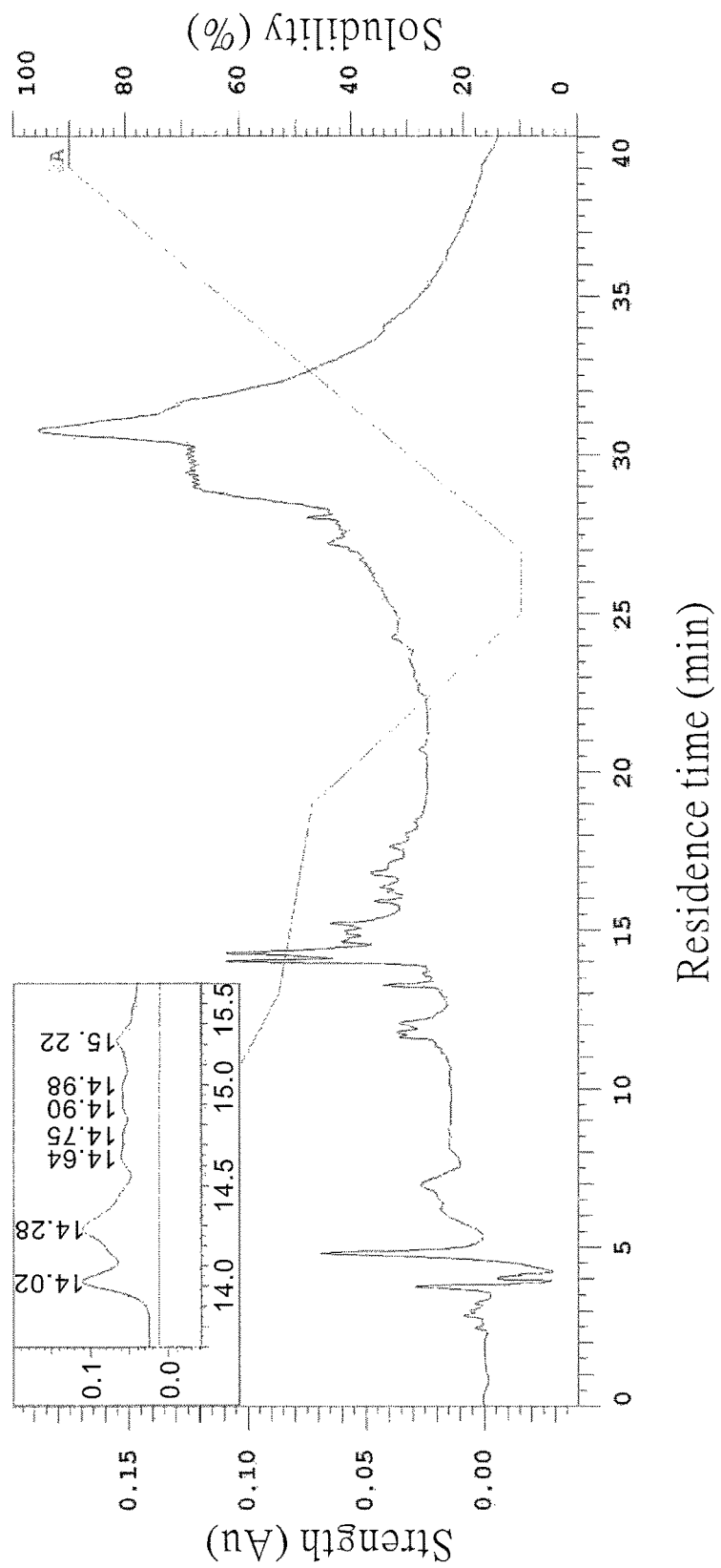
FIG. 2 is a reversed phase high performance liquid chromatography (RH-HPLC) of the crude product of the THLW peptide.
Figure 3:
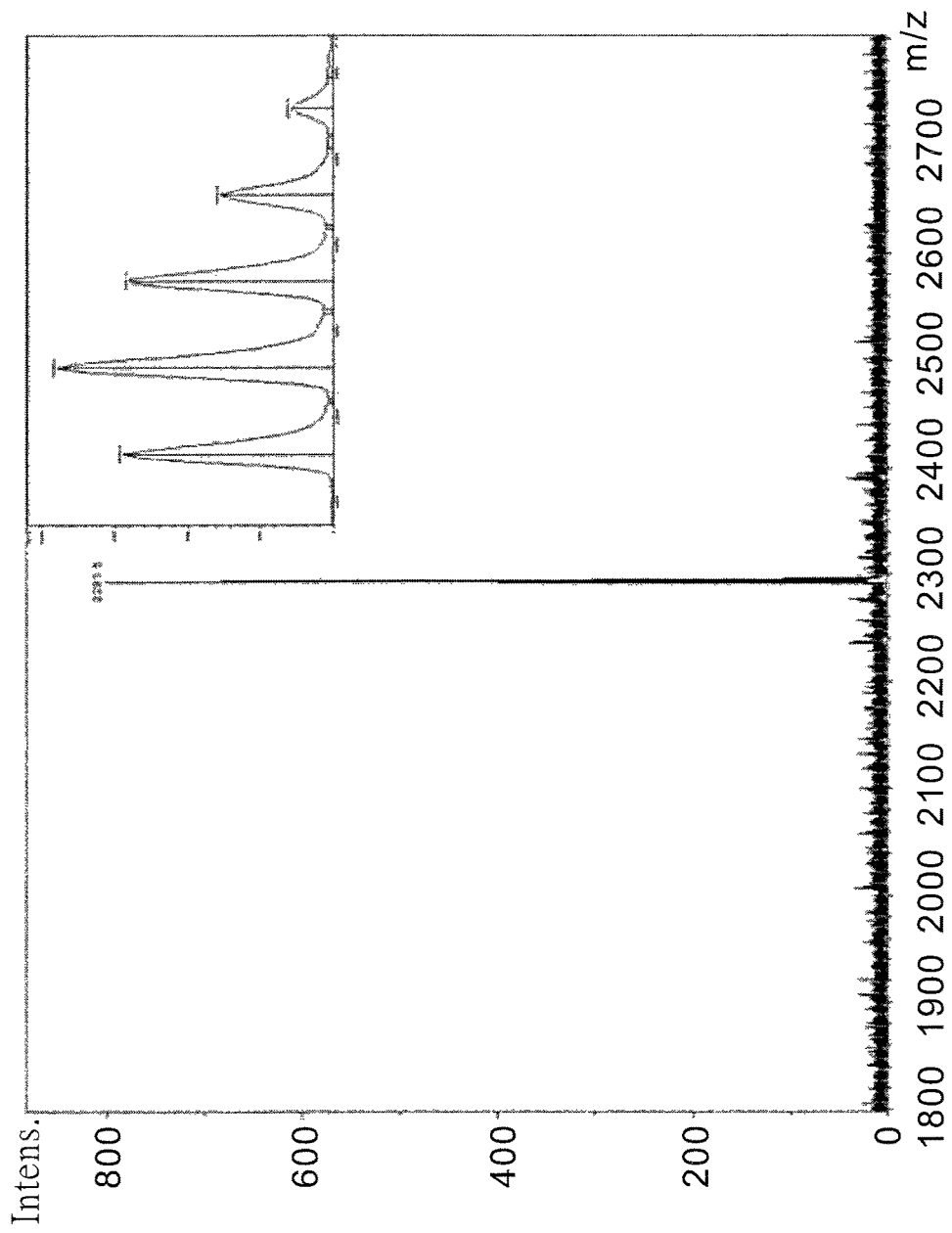
FIG. 3 is a mass spectrogram of a purified THLW peptide.
Figure 4:
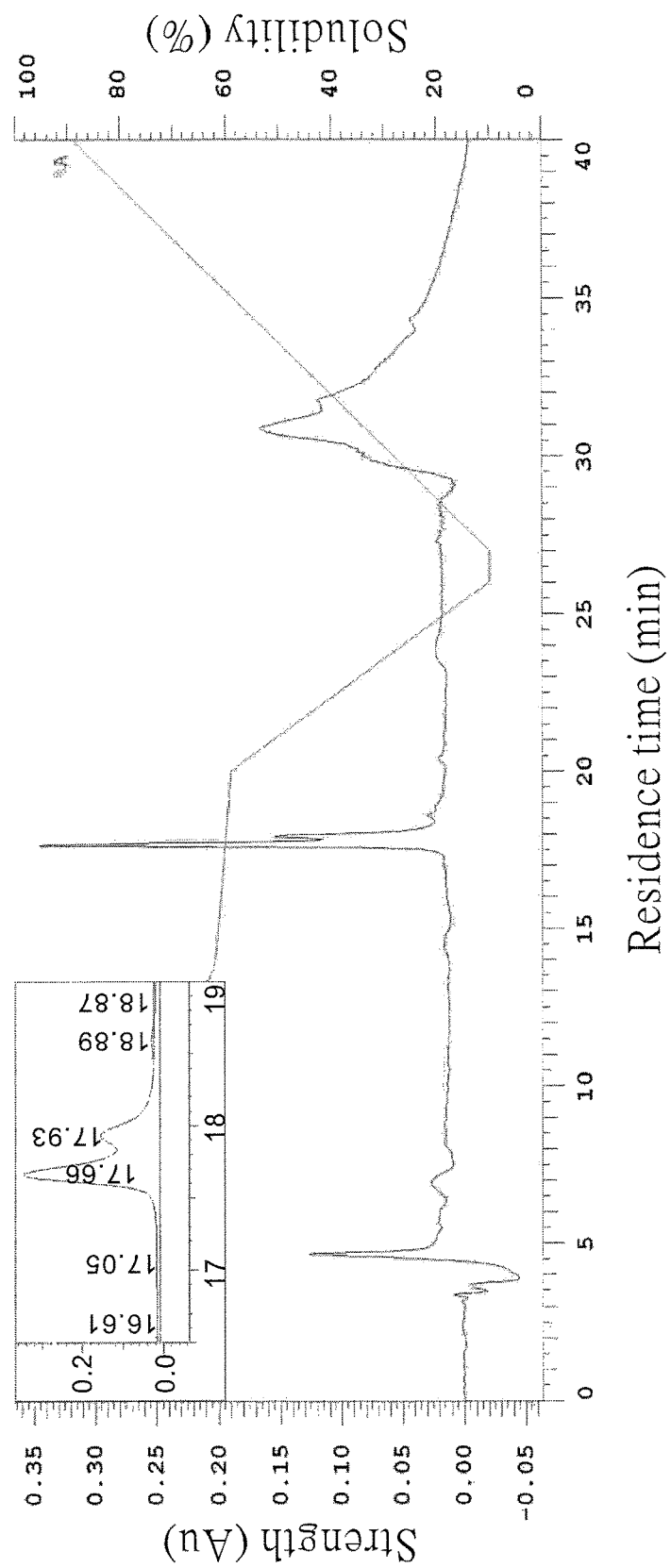
FIG. 4 is a RH-HPLC of the purified THLW peptide.

It was known from FIG. 2 that a residence time of the THLW peptide was approximately 14.02 min, a solution at such absorption peak was collected and freeze dried, and the molecular weight thereof was then identified by the MALDI-TOF mass spectrometer, in which, the operation process is the same as Example 1 and therefore will not repeatedly introduced herein. Identification results of the molecular weight were shown in FIG. 3, which indicated the purity and identification of the purified THLW peptide. Please refer to FIG. 4, the purified THLW peptide was freeze dried, dissolved, and analyzed by the RP-HPLC from which it was known that only the signal of the THLW peptide appeared.

It is known from the above results that the THLW peptide disclosed by the present application can be successfully synthesized and purified.

Example 3 Preparation of Polyclonal Antibodies

It should be firstly explained that this example was conducted according to the care of laboratory animals and specification of committee.

Leghorn chicken of satisfied age were selected, purified THLW peptide was used as the antigen, a first injection was prepared by mixing 150 µg of the antigen with 150 µL of a complete adjuvant at a ratio of 1:1 and then vigorously shaking a mixture to make the mixture achieve an emulsified state. A resulting mixed solution was discretely injected into different portions of chicken legs, and a second injection was performed 14 days after, and eggs were collected after four times of injections.

Yolk was collected from the egg, added with deionized water of equal volume, and mixed. Thereafter, 15 mL of chloroform was added, mixed, and centrifuged at a rotational speed of 4000 rpm for 5 min to collect a supernatant which contained the THLW antibodies. The supernatant was preserved at a temperature of −20° C., or the supernatant was dried into powder by using a freeze drying machine and then drily preserved for use in subsequent examples.

Figure 5:
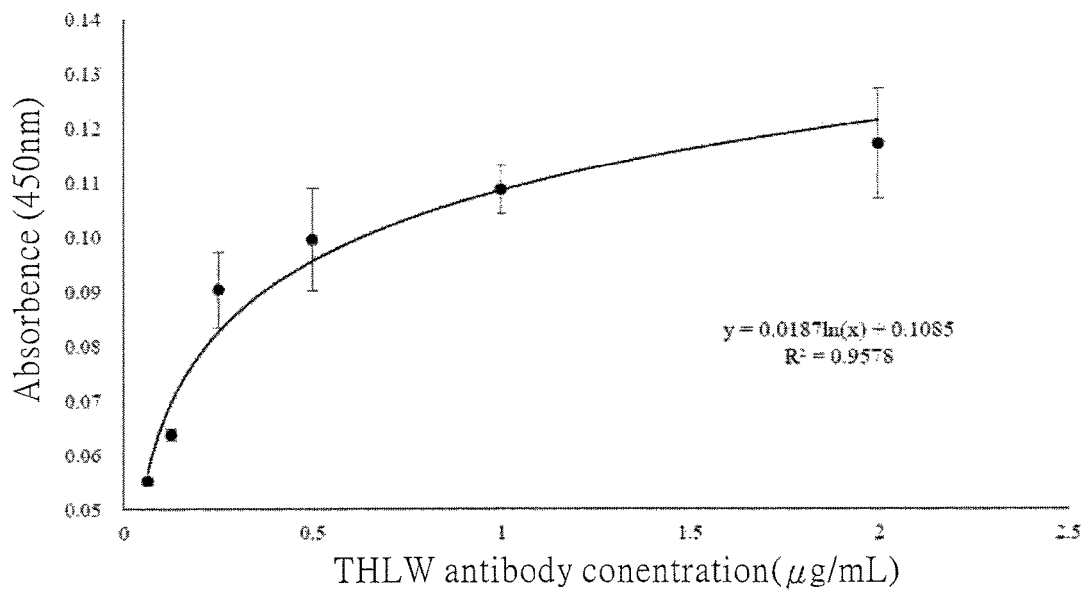
FIG. 5 illustrates detection results of reaction between a THLW peptide and a THLW antibody.

Example 4 Detection of Antibody Response Titer of Polyclonal Antibody with THLW Peptide Purified THLW peptide (0.2 mg/mL) was immobilized onto a well plate, THLW peptide that was not bond to the well plate was removed by washing. The THLW antibody prepared in Example 3 was diluted into concentrations of 1, 0.5, 0.25, 0.125, 0.0625 mg/mL based on a highest concentration of 0.2 mg/mL, reaction between the THLW peptide and the antibody was detected by indirect ELASA, result of which was shown in FIG. 5. It was known from FIG. 5 that the immunoreaction between THLW antibody at a concentration of from 0.0625 mg/mL to 0.25 mg/mL and the THLW peptide had dose association, therefore the THLW antibody was further sequentially diluted into concentrations of 125, 62.5, 31.2515.625, 738125, 3.90625, and 1.953125 µg/mL, etc., then enzyme-linked immunosorbent assay (ELISA) was used to detect the antibody-antigen reaction, result of which was shown in FIG. 6.

Figure 6:
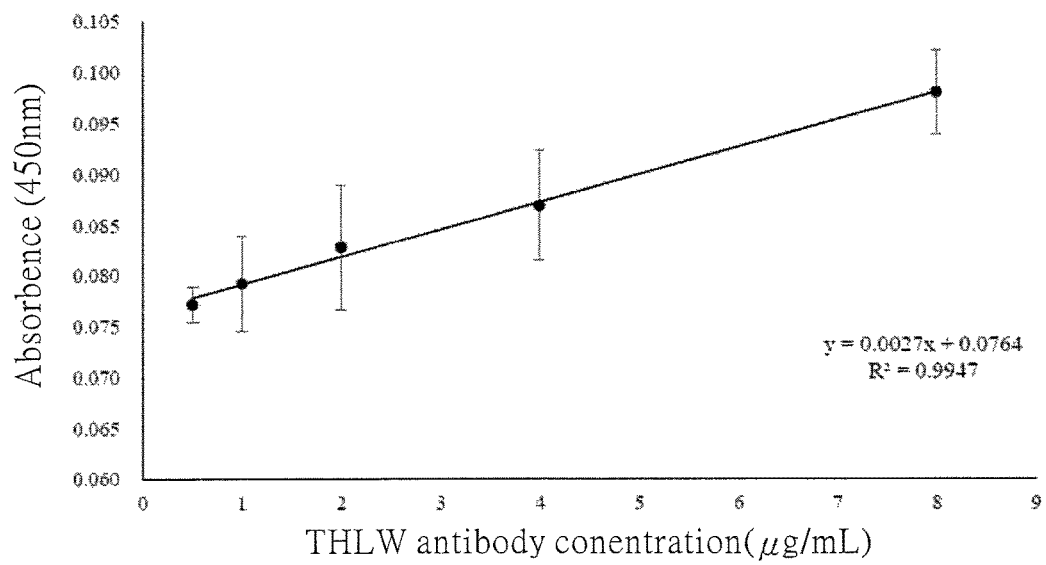
FIG. 6 illustrates analysis results of reaction between the THLW peptide and the THLW antibody.

It was clearly shown in FIG. 6 that the THLW antibody has good linear relation with the THLW peptide.

Example 5 Collecting Saliva Specimen

Saliva specimens were collected from healthy subjects and oral cancer patients, and the providers were inhibited from eating anything one hour before collecting the saliva specimens. The collected saliva specimens were respectively added with an enzyme inhibitor, then centrifuged at 3000 rpm under 4° C., and a supernatant was collected for use in subsequent examples.

Example 6 Determination of Protein Concentration

In this example, protein concentration in the saliva specimen was determined by using bicinchoninic acid (BCA) assay.

Figure 7:
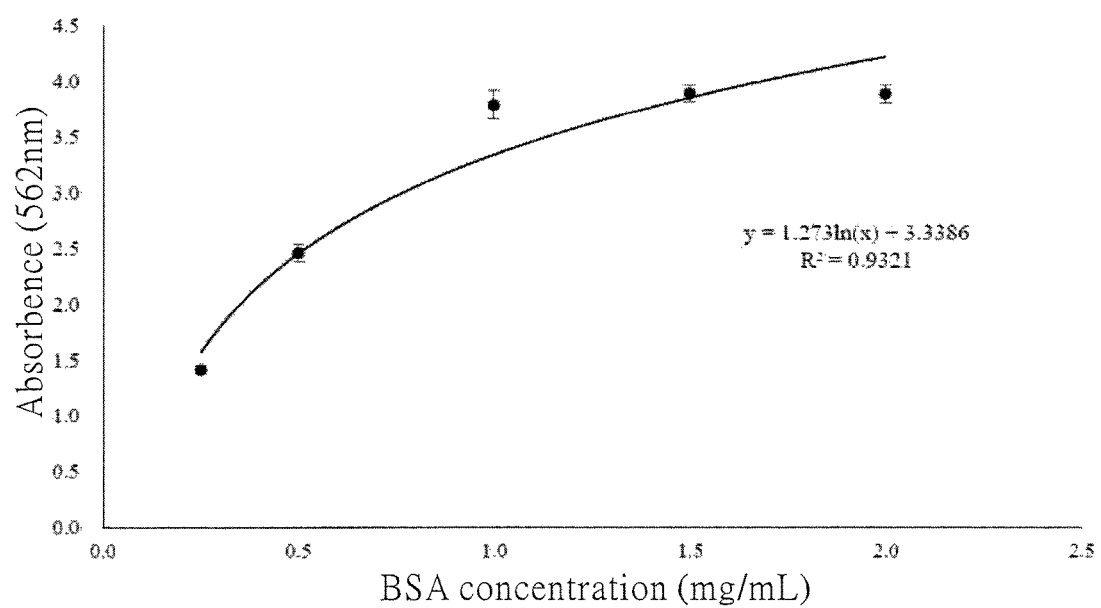
FIG. 7 is a standard curve of protein concentration constructed by a bovine serum albumin (BSA) standard.

First, BSA standards with final concentrations of 2, 1.5, 1, 0.5, and 0.25 mg/mL were used to construct a standard curve of protein concentration, as shown in FIG. 7.

Figure 8:
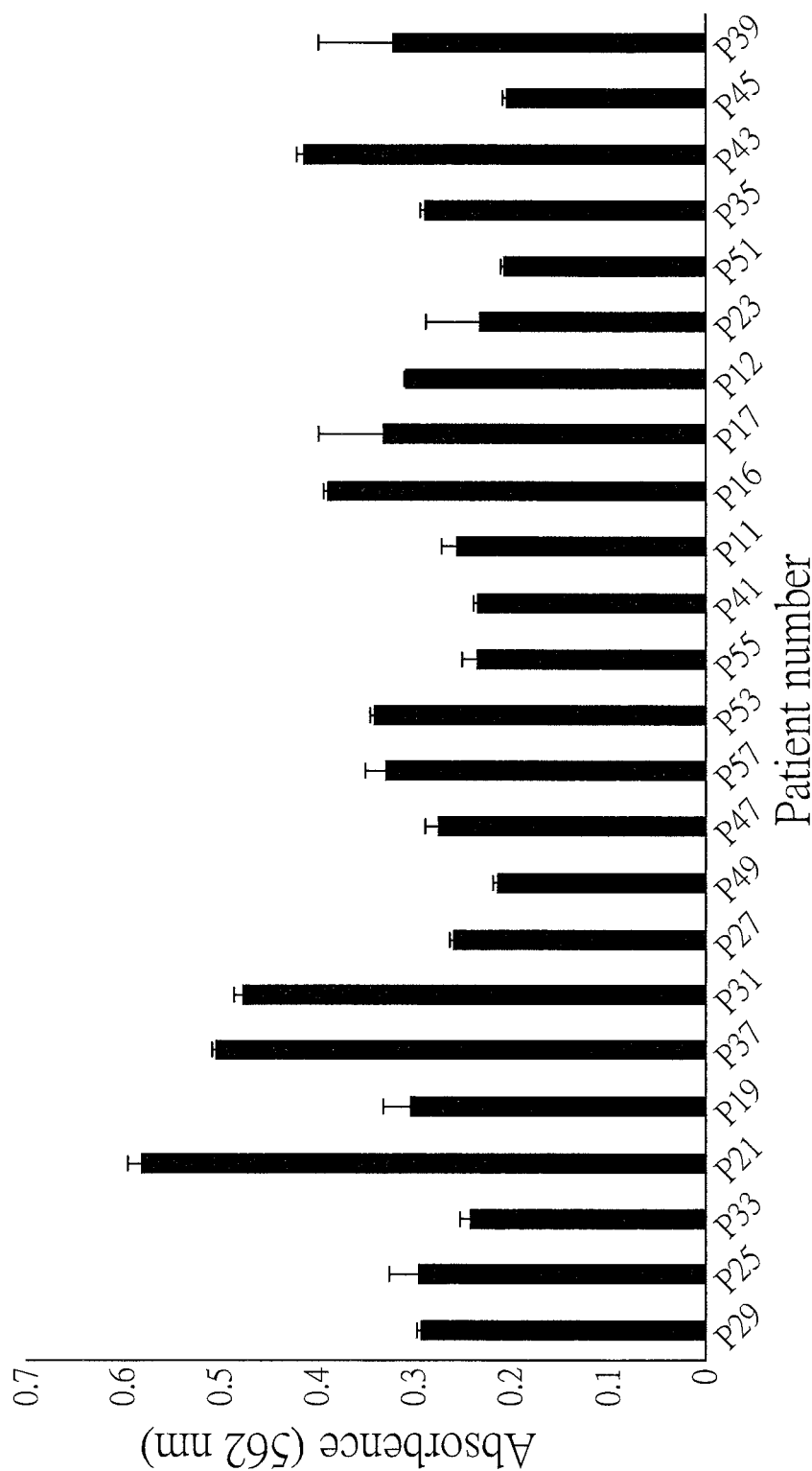
FIG. 8 is detection results of total protein concentrations in various saliva specimens.

Saliva specimens provided by diagnosed oral cancer patients were diluted one-fold, and a total protein concentration of each specimen was quantified by the BCA assay, result of which was shown in FIG. 8.

Example 7 Biosensor

Commercially available CM5 sensing chip was selected, a chip surface was firstly activated by EDC/NHS and then covalently bond with a biomarker of a preset concentration, after the attachment of the biomarker, remaining activated portions were covered by EA, thereby acquiring the sensing chip.

In this example, the THLW peptide, the THLW antibody, protein E6, and anti-protein E6 antibody were used as biomarkers to prepare the sensing chips. Before being used to prepare the sensing chip, bonding conditions of the biomarkers were firstly tested using sodium acetate solutions at pH values of 3.5, 4.0, 4.5, 5.0, and 5.5, respectively, and it was determined that the pH value of 3.5 enables the biomarker to have the maximum binding quantity, and therefore the binding of the biomarkers were conducted in such condition. In addition, in this example, the concentration of the THLW peptide was 3.3 µM, and the concentration of the THLW antibody was 0.2 µg/mL, the concentration of the protein E6 was 0.03 µg/mL, and the concentration of the anti-protein E6 antibody was 10 µg/mL.

Example 8 First Detection Using Biosensor

Saliva specimens were respectively collected from 12 oral cancer subjects and 10 healthy subjects. Each saliva specimen was respectively diluted 2-fold and 8-fold, and then reacted with the protein E6 sensing chip, results of which were shown in FIGS. 9-10.

Figure 9:
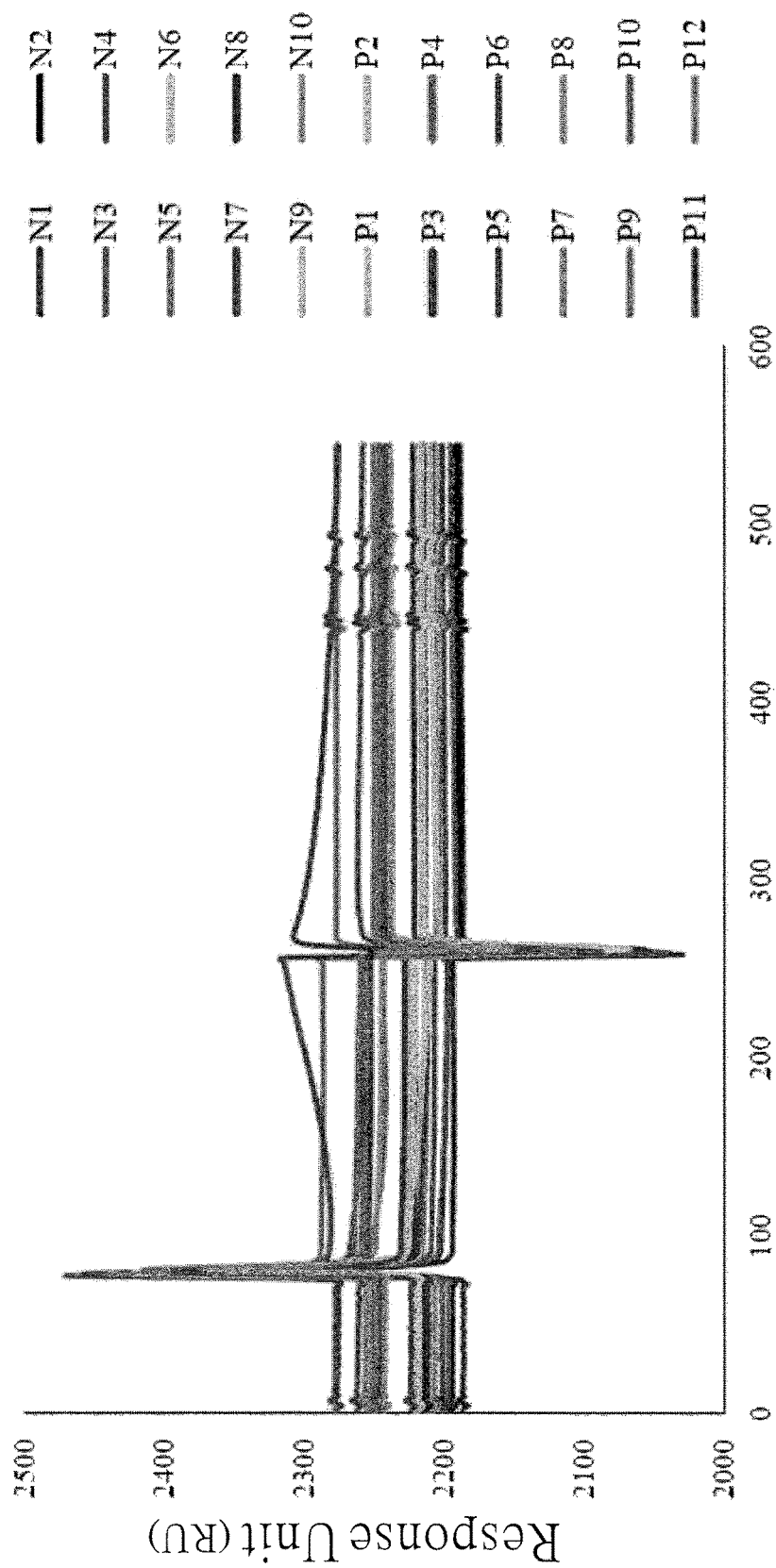
FIG. 9 is results of reaction of each 2-fold diluted saliva specimen using a protein E6 sensing chip.

It was known from FIG. 9 that substances in the saliva specimens from the oral cancer subjects would have a relatively great interacting force with the protein E6, which was approximately 2300 RU (response unit), that is, a protein that would have interaction with the protein E6 existed in the saliva specimens of the oral cancer subjects. Therefore, it could be inferred that the oral cancer subjects had been infected by the HPV-16, and anti-protein E6 antibody has been produced in vivo.

Figure 10:
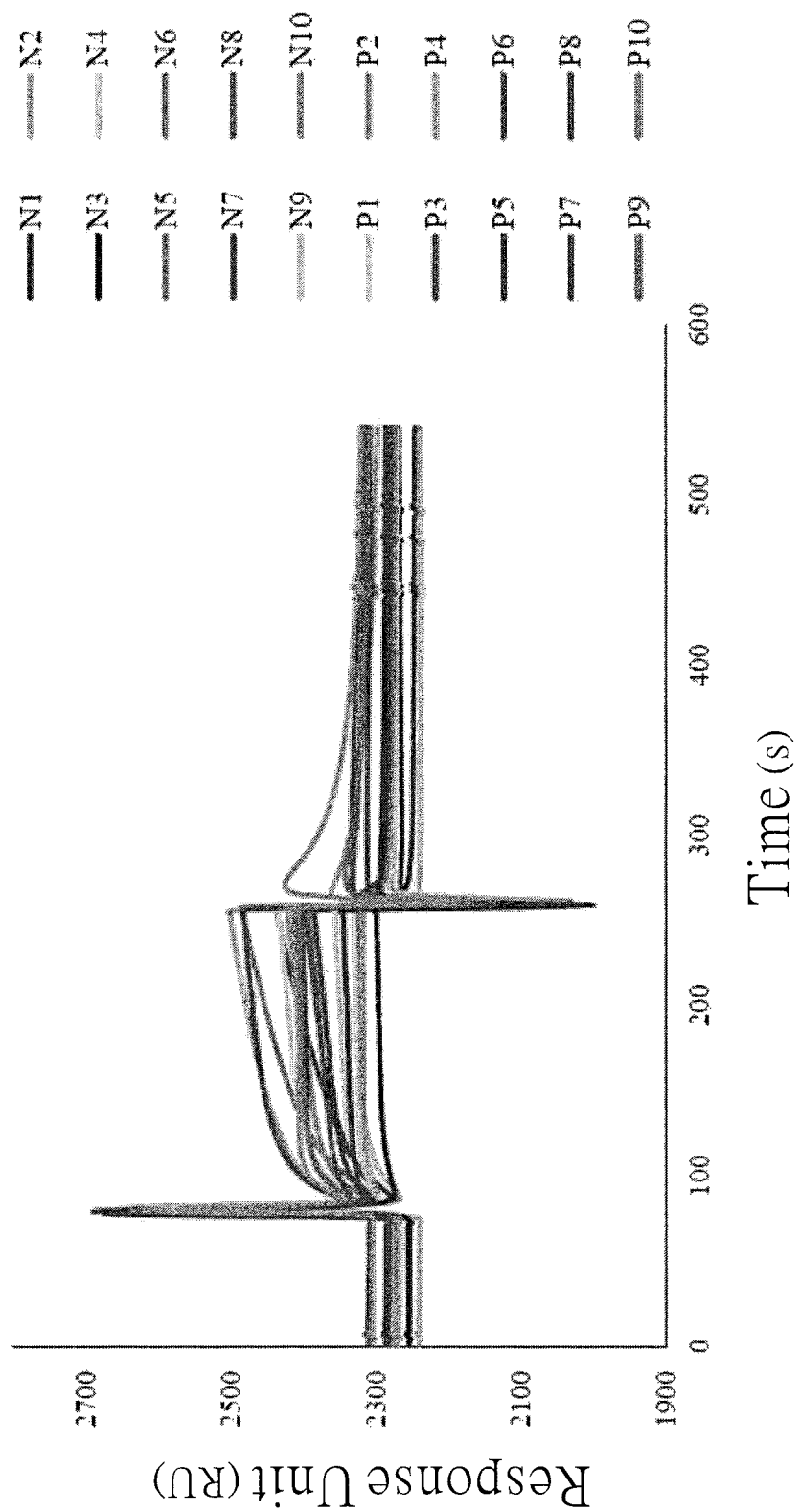
FIG. 10 is results of reaction of each 8-fold diluted saliva specimen using the protein E6 sensing chip.

Besides, as shown in FIG. 10, although sensing curves of the saliva specimens from both the healthy subjects and the oral cancer subjects rose over time, the saliva specimens based on the oral cancer subjects contained the substances that would have interaction with the protein E6, therefore, the rising amplitude in such specimens would be obviously higher than specimens from the healthy subjects.

It can be known from the above that when the subjects are infected with the HPV-16 and saliva specimens therefrom are detected to contain the protein E6, the subjects are a high risk group of developing the oral cancer. In other words, by detecting the response of the saliva specimens, it can be inferred whether the subjects have the risk of developing the oral cancer.

Example 9 Second Detection Using Biosensor

Figure 11:
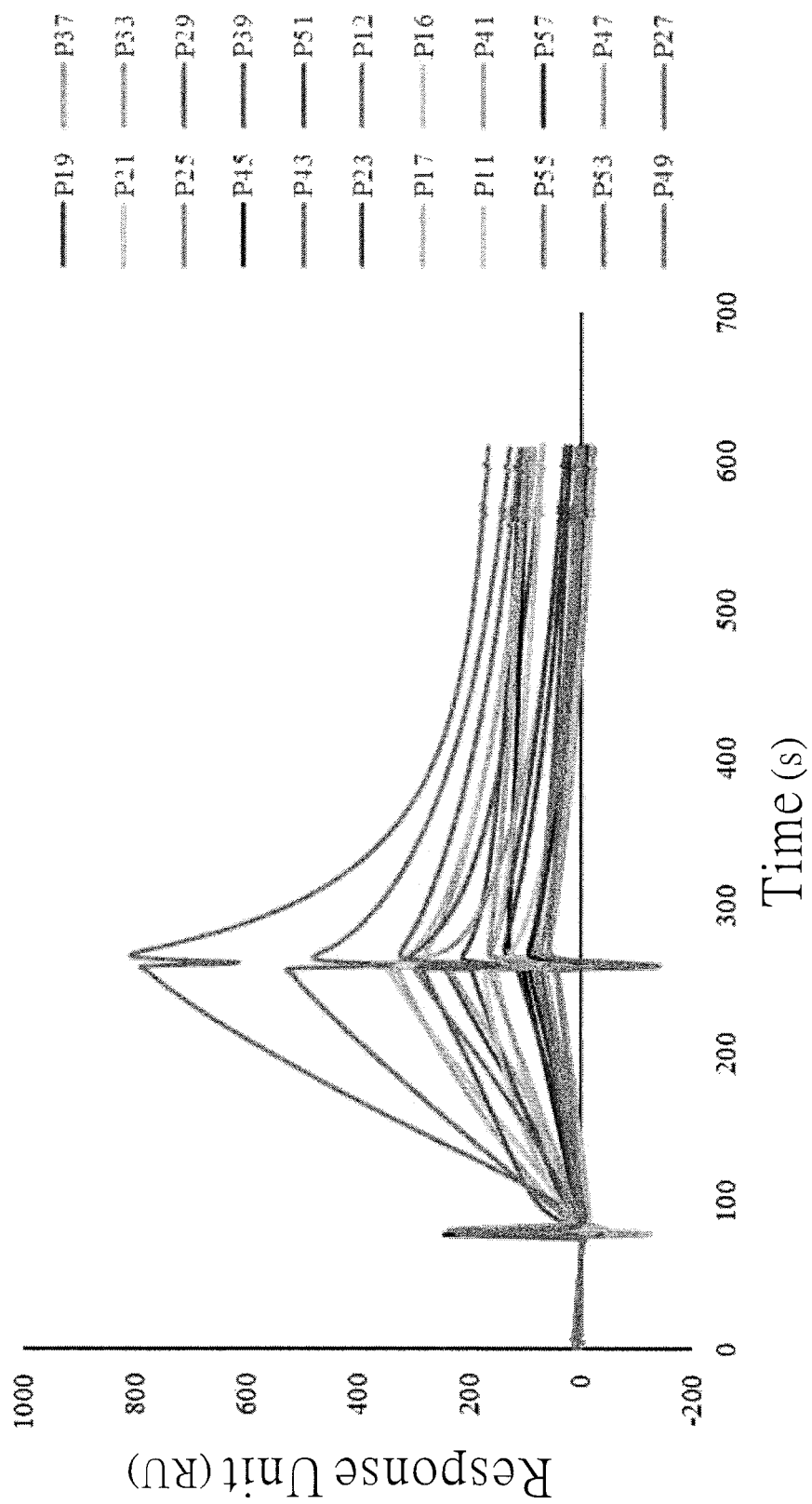
FIG. 11 is results of reaction between each 2-fold diluted saliva specimen and the protein E6 sensing chip.
Figure 12:
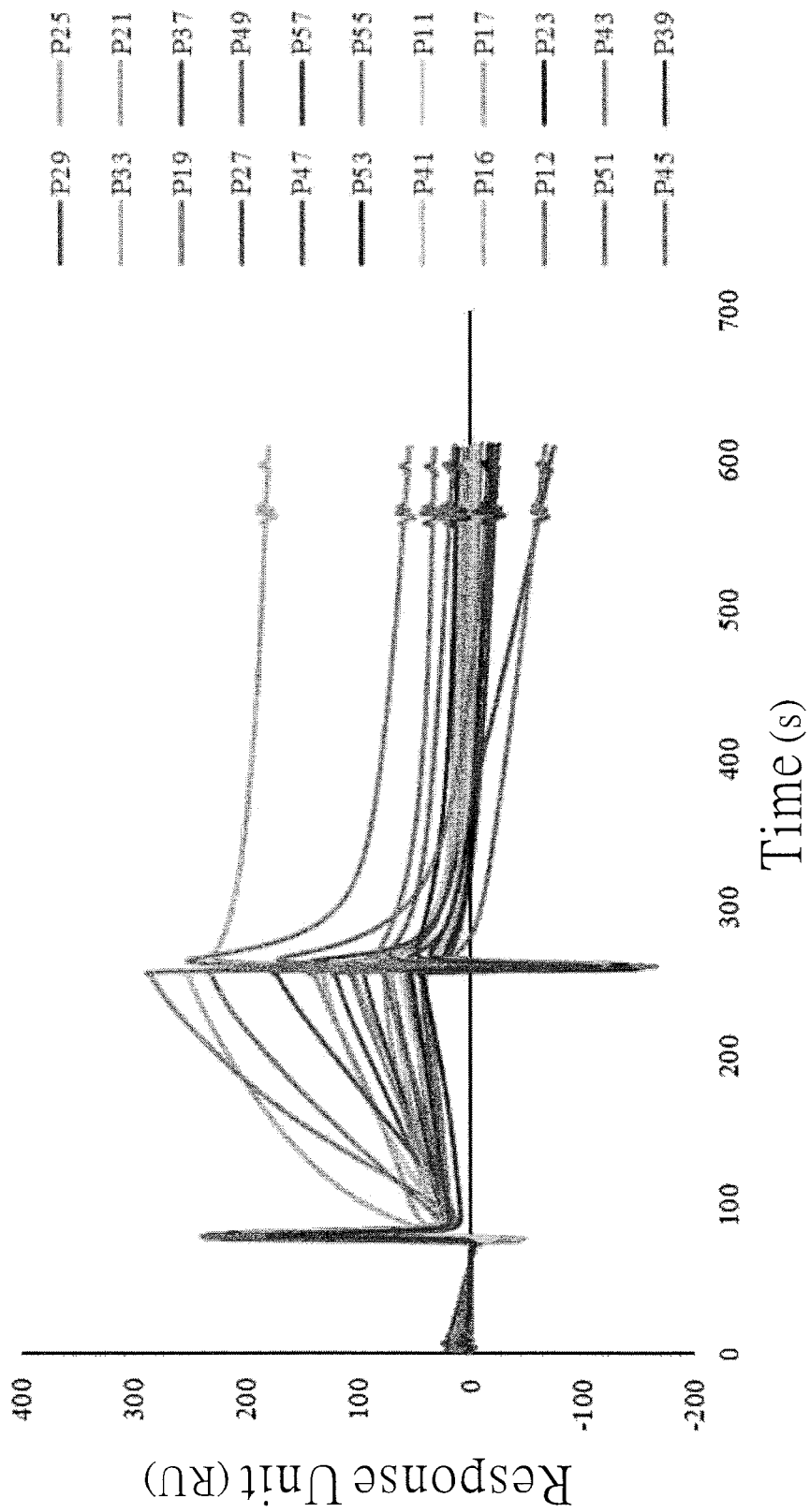
FIG. 12 is results of reaction between each 2-fold diluted saliva specimen and a THLW peptide sensing chip.

Saliva specimens from 22 patients with stage IV oral cancer were diluted 2-fold, then respectively reacted with the THLW peptide sensing chip and the protein E6 sensing chip, and sensing curves were respectively detected, results of which were shown in FIG. 11 and FIG. 12.

As shown in FIG. 11, because a part of substances of the saliva specimens had relatively large interactive force with the protein E6, it was shown that such specimens have antibodies corresponding to the protein E6. It could be inferred that the oral cancer patients who provided such specimens had high probability of being infected by the HPV-16, the protein E6 was enabled to produce immunoreaction in vivo, and the existence of the antibodies corresponding to the protein E6 was therefore detected in vivo.

Compared FIG. 11 with FIG. 12, most part of the substances of the saliva specimens in FIG. 12 had interactive force with the THLW peptide, which was the same as that of FIG. 11, it was shown that the THWL peptide disclosed by the present application could replace the protein E6 and be the biomarker for predicting the risk of developing the oral cancer.

Example 10 Third Detection Using the Sensing Chip

Figure 13:
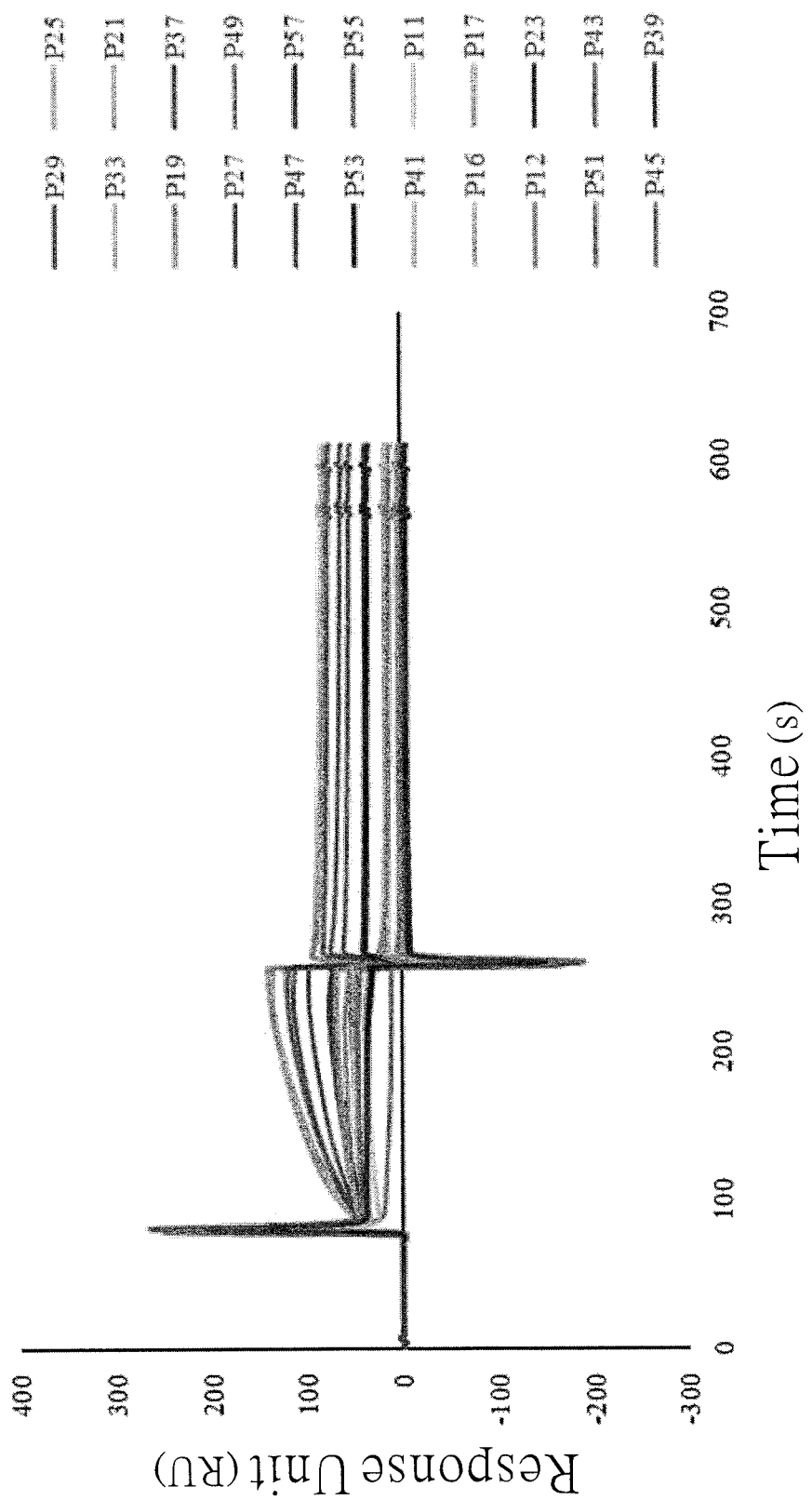
FIG. 13 is results of reaction between each saliva specimen after treatment and 3-fold dilution and the THLW peptide sensing chip.

THLW was firstly used to be premixed with each of the 3-fold diluted saliva specimens for 1 hr, then a mixture was allowed to react with the THLW peptide sensing chip, results of which were shown in FIG. 13, indicating that the signal of the sensing chip which contained the THLW peptide disclosed by the present application was stable.

It was known that the THLW peptide disclosed by the present application could be effectively used as a biomarker for detecting the risk of developing the oral cancer.

Example 11 Fourth Detection of the Sensing Chip

Figure 14:
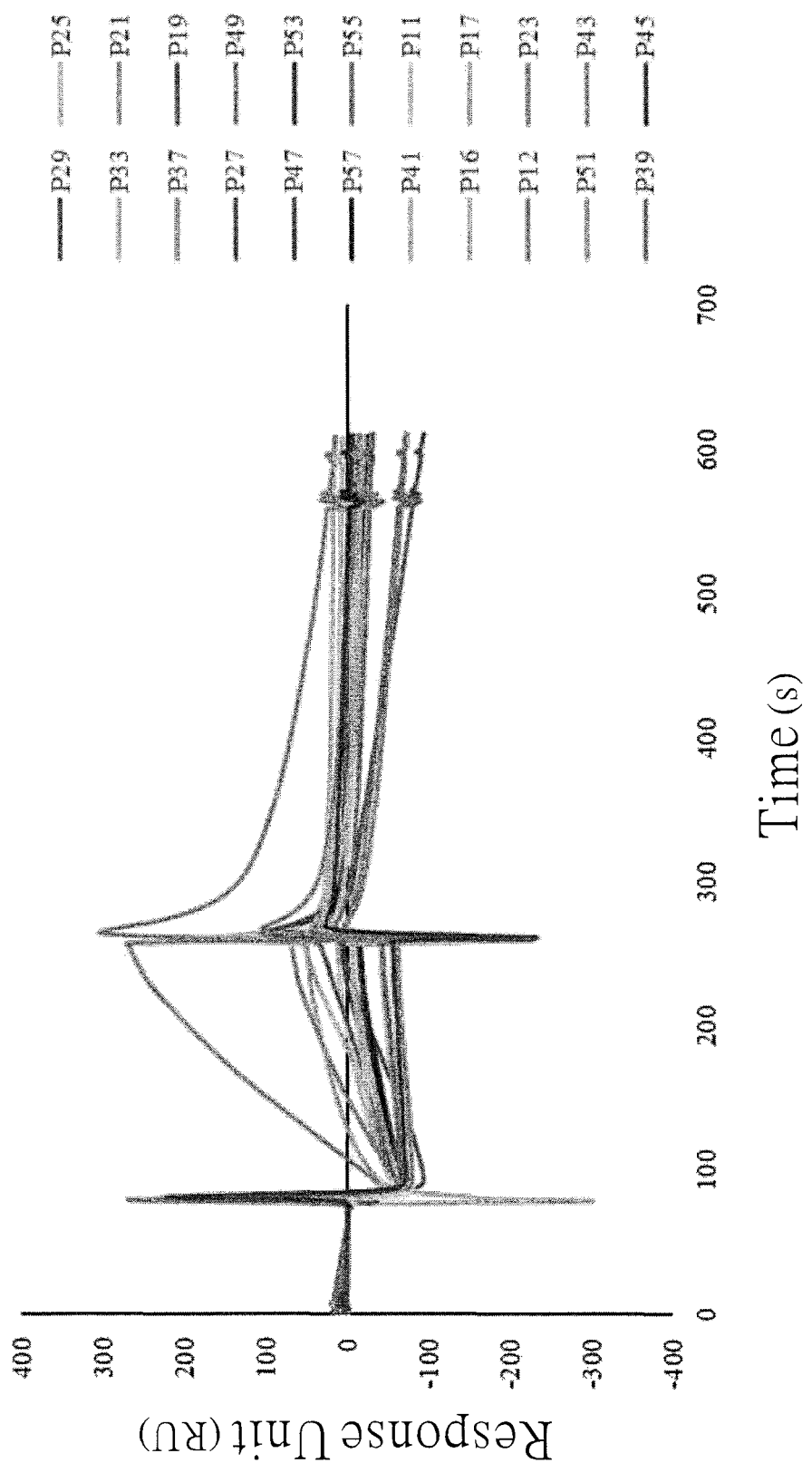
FIG. 14 is results of reaction between each 2-fold diluted saliva and the THLW peptide sensing chip.

Saliva specimens from 22 patients were diluted 1-fold, then respectively reacted with the THLW peptide sensing chip, and detection results were shown in FIG. 14.

It was known from the results of FIG. 14 that the saliva specimens provided by the patient infected with the HPV-16 contained the substances that could react with the THLW antibody, thus the substances could be detected because their relatively great interactive force with the THLW antibodies.

In other words, the THLW antibodies prepared by using the THLW antigen disclosed by the present application can be used in predicting whether the specimen provider belongs to a high risk group of developing the oral cancer.

Example 12 Competitive ELISA

Figure 15:
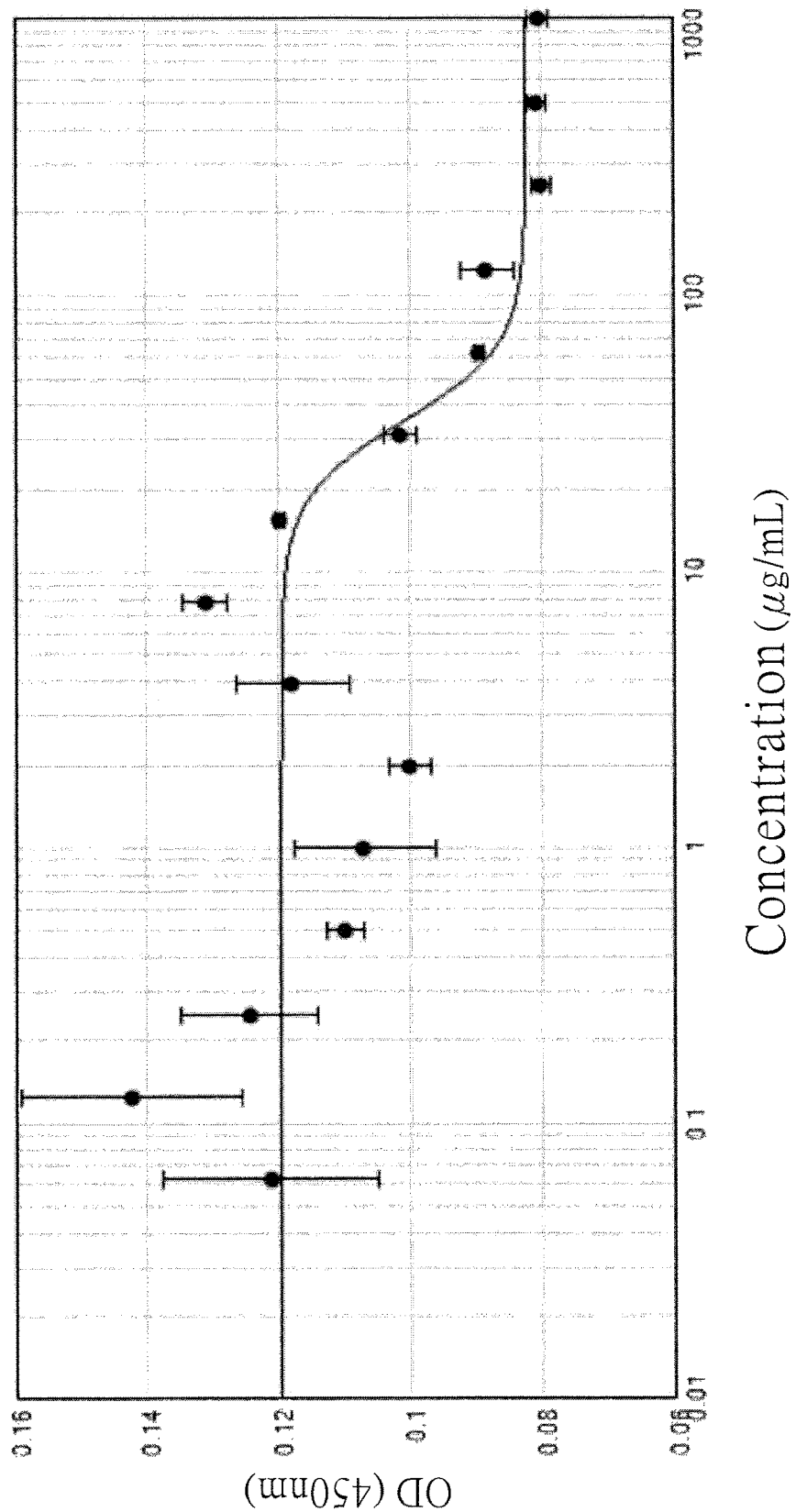
FIG. 15 is a standard competition curve constructed by using the THLW peptide as an antigen.

Purified THLW peptide (0.2 mg/mL) was immobilized onto a well plate, THLW peptides that were serially diluted were used as the antigens and premixed with the THLW antibody having a concentration of 125 µg/mL for competing, so as to construct a standard competitive curve, which was shown in FIG. 15.

It was known from results of FIG. 15 that an obvious concentration correlation was presented within a concentration range of between 15.625 and 62.5 μg/mL, which indicated that the standard curve in future could be used to quantitate a target protein whose concentration is within such range, in other words, to calculate a content of a correct antigen in the specimen.

Example 13 Affinity Analyses of THLW Antibodies

THLW antibodies and anti-E6 monoclonal antibodies, both of which were diluted into serial concentrations, were used as analytes. A highest concentration was 10.00 μg/mL, which was respectively serially diluted into 5.00 μg/mL, 3.33 mg/mL, 2.50 mg/mL, 2.00 mg/mL, 1.66 μg/mL, and other concentrations, then reacted with protein E6 which was immobilized onto a chip, and detection was performed, results of which were shown in FIG. 16 and FIG. 17. Thereafter, 1:1 binding mode was used to conduct kinetic analyses, results of which are shown in Tables 1-2.

TABLE 1

Kinetic analysis of reaction between a sensing chip immobilized with protein E6 and anti-E6 monoclonal antibodies of different concentrations

| Association rate $k_a$ (1/Ms) | Dissociation rate constant $k_d$ (1/s) | Equilibrium dissociation constant $K_D$ (M) | Rmax (RU) | tc | Chi$^2$ (RU$^2$) |
|---|---|---|---|---|---|
| $1.103 \times 10^4$ | 0.03205 | $2.905 \times 10^{-4}$ | $1.152 \times 10^4$ | $7.328 \times 10^5$ | 3.90 |

TABLE 2

Kinetic analysis of reaction between a sensing chip immobilized with protein E6 and THLW antibodies of different concentrations

| Association rate $k_a$ (1/Ms) | Dissociation rate constant $k_d$ (1/s) | Equilibrium dissociation constant $K_D$ (M) | Rmax (RU) | tc | Chi$^2$ (RU$^2$) |
|---|---|---|---|---|---|
| 340.6 | $1.191 \times 10^{-4}$ | $3.497 \times 10^{-7}$ | 1385 | $8.020 \times 10^6$ | 0.524 |

Figure 16:
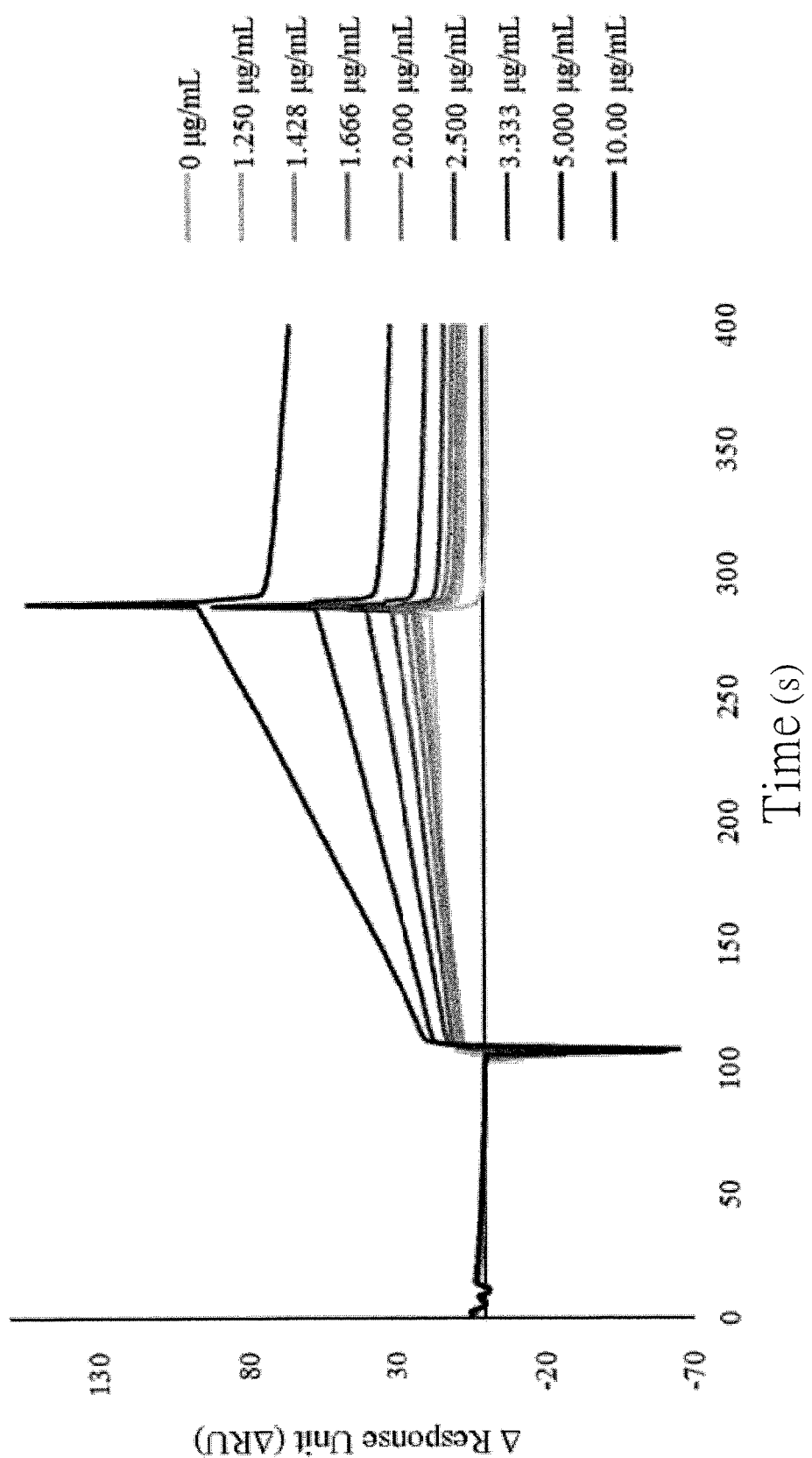
FIG. 16 is surface plasmon resonance (SPR) sensing spectra between a chip immobilized with the protein E6 and anti-E6 monoclonal antibodies of different concentrations.
Figure 17:
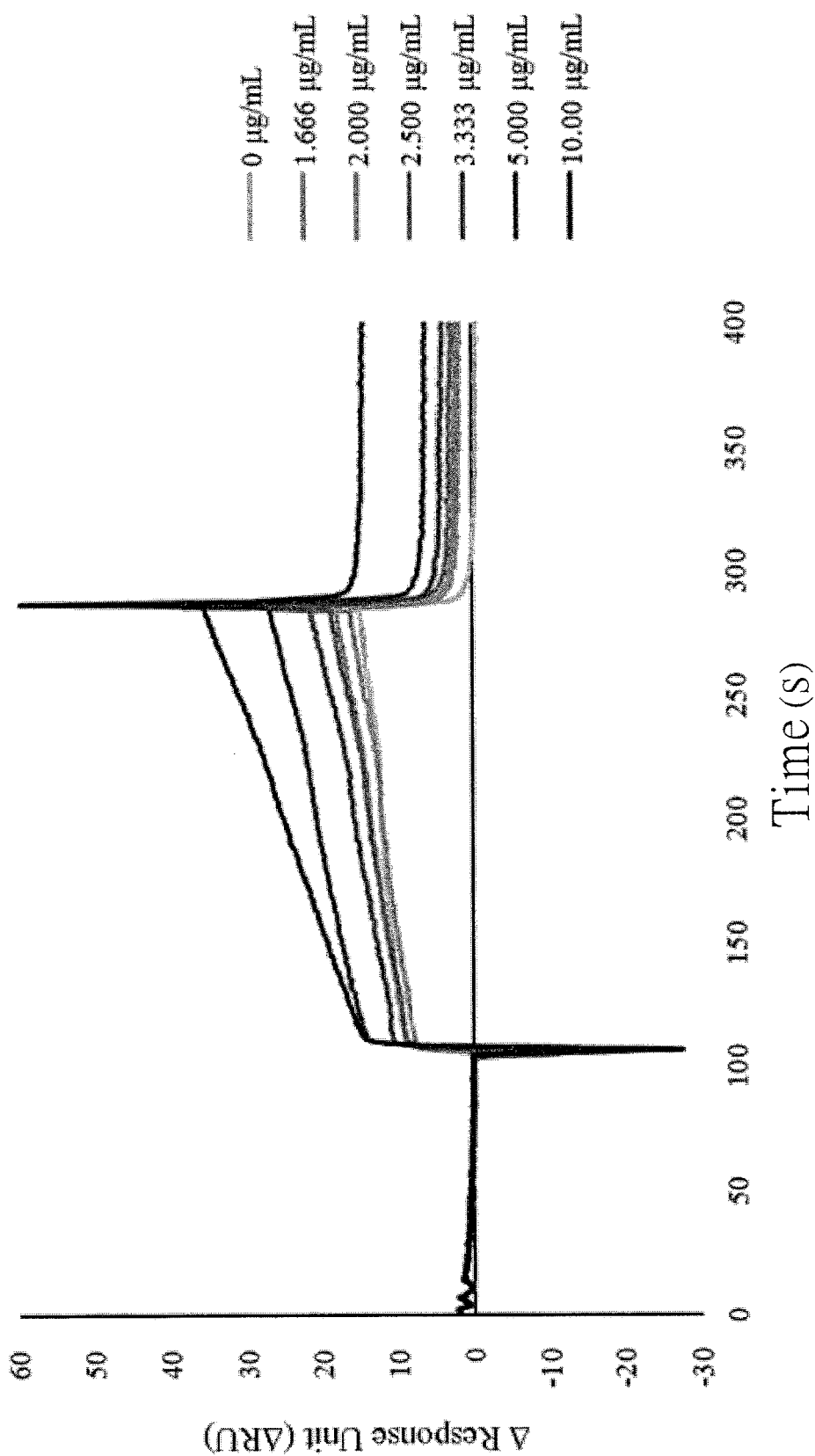
FIG. 17 is SPR sensing spectra between the chip immobilized with the protein E6 and THLW antibodies of different concentrations.

It was known from results of FIG. 16 and FIG. 17 that both the anti-E6 monoclonal antibody and the THLW antibody make the RU change, besides, ARU tends to rise with the higher concentrations of the antibody.

Figure 18:
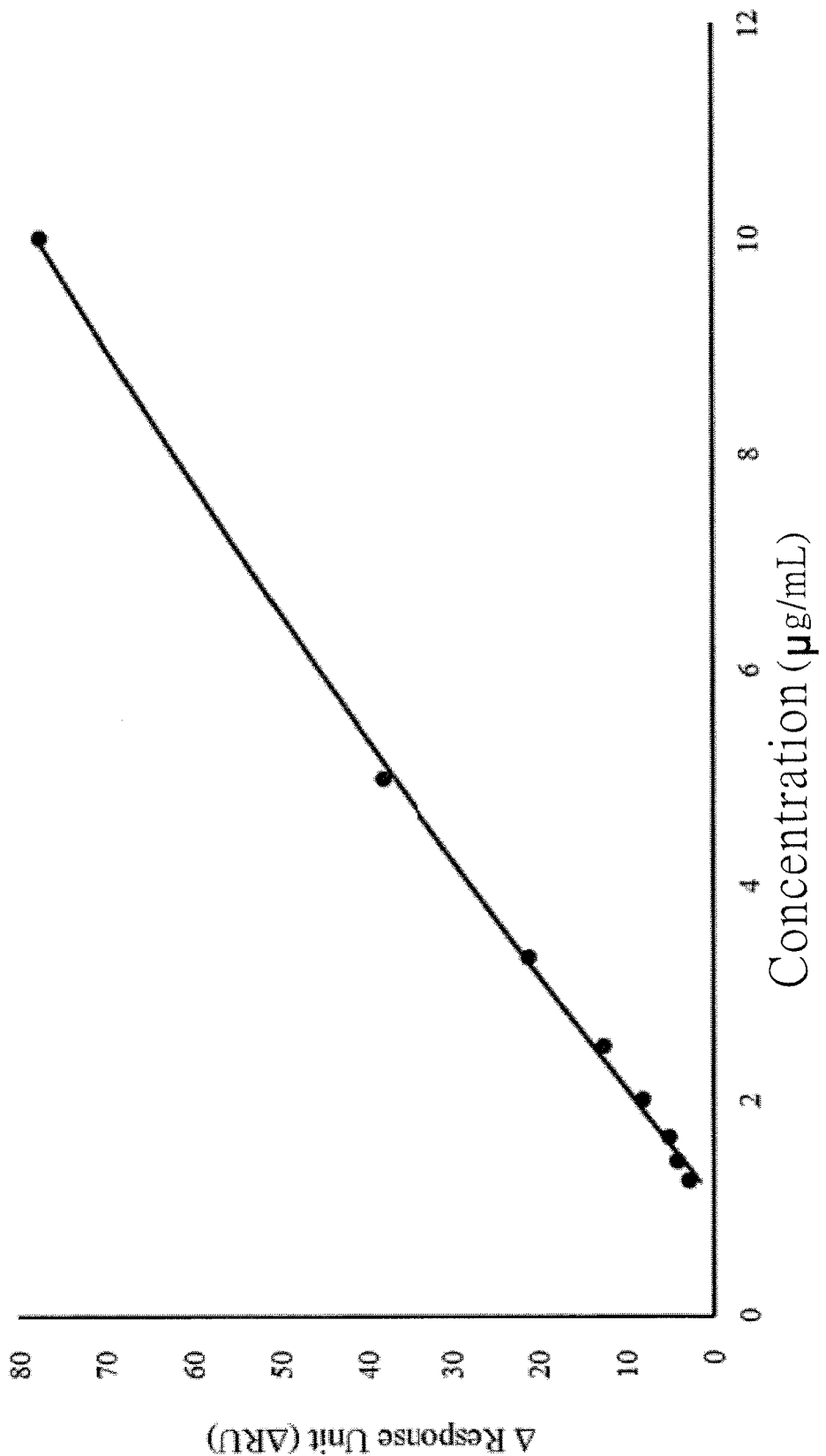
FIG. 18 is results of reaction between the chip immobilized with the protein E6 and the anti-E6 monoclonal antibodies of different concentrations.
Figure 19:
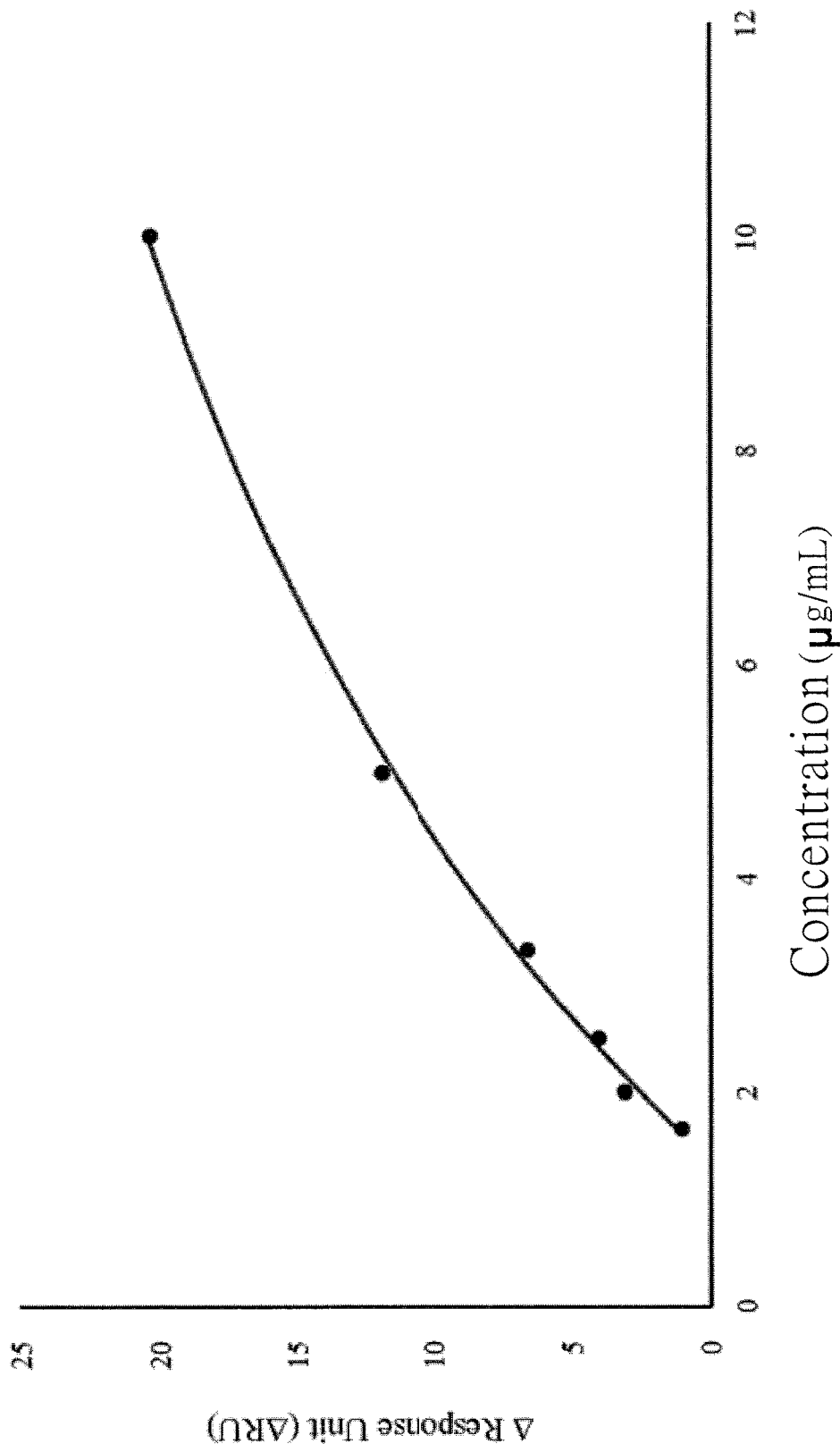
FIG. 19 is results of reaction between the chip immobilized with the protein E6 and the THLW antibodies of different concentrations.
Figure 20:
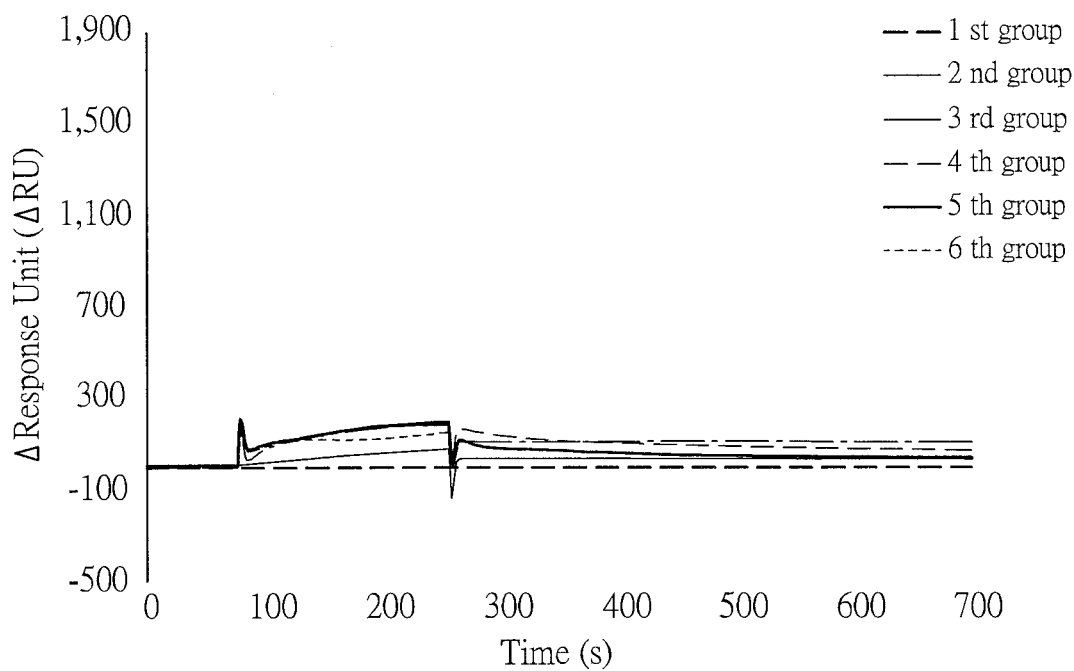
FIG. 20 is analyses of binding forces between the anti-E6 monoclonal antibody and saliva specimens.
Figure 21:
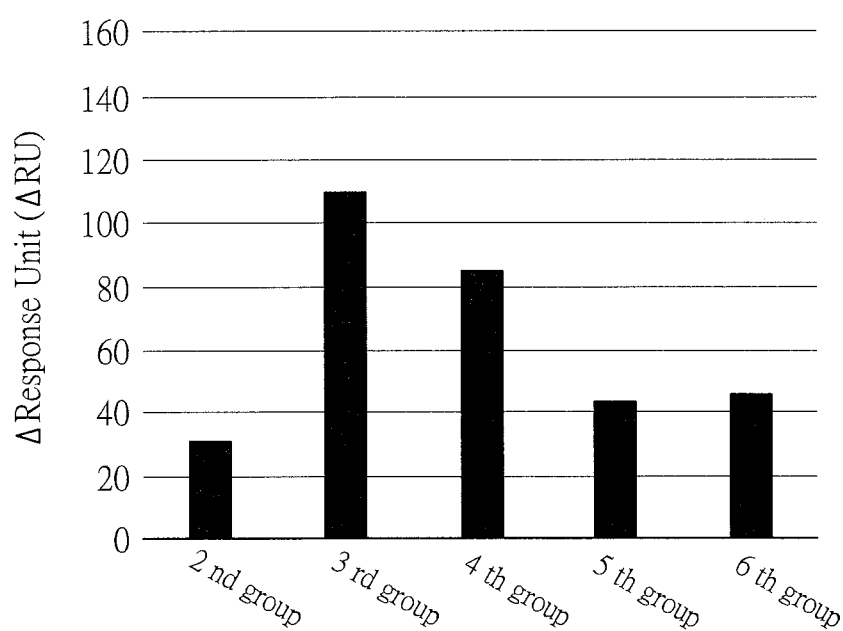
FIG. 21 is results of variation of response unit (RU) value after reaction between the anti-E6 monoclonal antibody and different saliva specimens.
Figure 22:
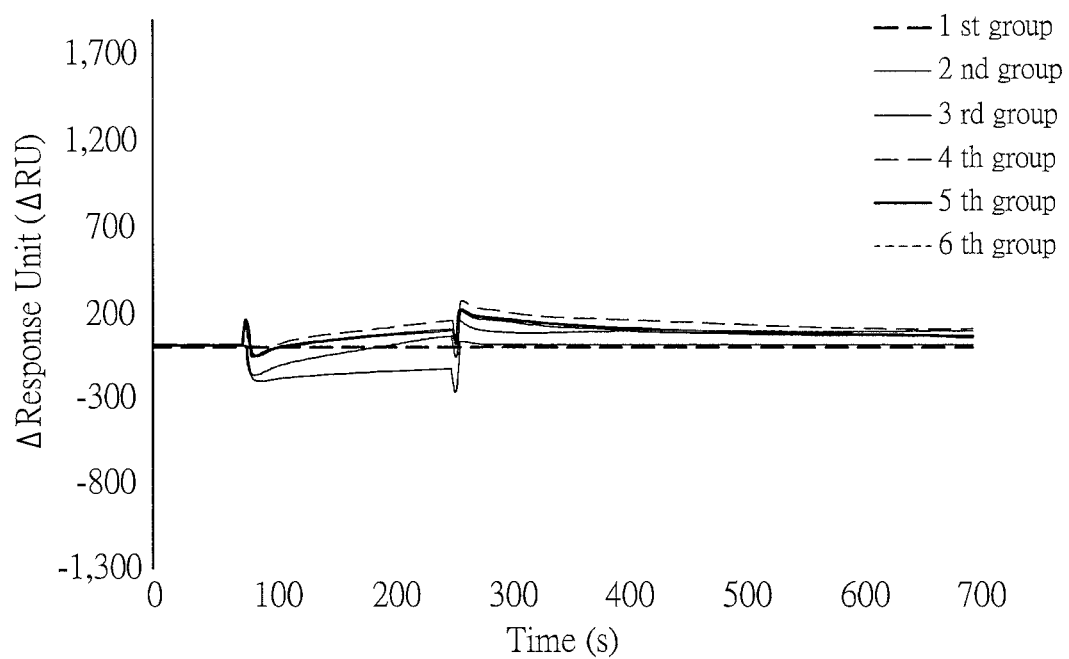
FIG. 22 is analyses of binding forces between the THLW antibody and saliva specimens.
Figure 23:
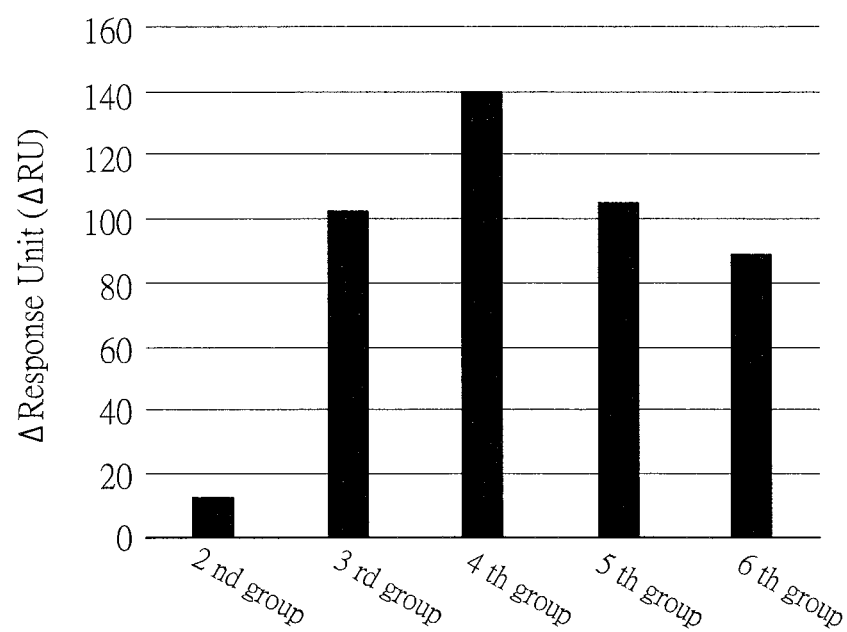
FIG. 23 is results of variation of RU value after reaction between the THLW antibody and different saliva specimens.

Further, when the chip passes through anti-E6 monoclonal antibody and the THLW antibody of different concentrations, and highest ARUs achieved and corresponding concentrations were analyzed, results of which were shown in FIG. 18 and FIG. 19, and affinity analysis results were listed in Table 3.

TABLE 3

Affinity analyses between sensing chip immobilized with protein E6 and antibody of different concentrations

| Antibodies | Anti-E6 monoclonal antibody | THLW antibody |
|---|---|---|
| $K_D$ (M) | $1.091 \times 10^{-6}$ | $1.753 \times 10^{-7}$ |
| Rmax (RU) | 621.7 | 52.94 |
| Offset (RU) | −11.11 | −6.557 |
| Chi$^2$ (RU$^2$) | 1.40 | 0.288 |

It was known from the above results that the antibody of the THLW peptide disclosed by the present application has good affinity with the HPV and effect thereof is similar to the anti-E6 monoclonal antibody, therefore, the THLW peptide disclosed by the present application can be used as a tool of detecting the risk of oral cancer.

Example 14 Analysis of Binding Forces of THLW Antibody

Specimens from 11 non-oral cancer patients and 5 oral cancer patients were collected, and divided into groups according to the following conditions: a first group was a blank control group, which was only a phosphate buffer; a second group was specimens from the non-oral cancer patients which was diluted one-fold with the phosphate buffer; a third group was specimens from the oral cancer patients which was diluted one-fold with the phosphate buffer; a fourth group was specimens from the oral cancer patients which was added with an equal volume of the protein E6 having a concentration of 0.01 μg/mL; a fifth group was specimens from the oral cancer patients which was added with an equal volume of the protein E6 having a concentration of 0.16 μg/mL; and a sixth group was specimens from the oral cancer patients which was added with an equal volume of the protein E6 having a concentration of 0.5 μg/mL.

The THLW antibody and the anti-E6 monoclonal antibody were respectively immobilized onto a separate chip, to test the change of the RU value and sensing results of specimens from different groups, results of which were shown in FIGS. 20-23.

It was known from the FIGS. 20-23 that no matter the anti-E6 monoclonal antibody or the THLW antibody was used to conduct the detection, the RU variation of the second group was obviously lower than the RU variation of the third group, that is, the THLW antibody indeed can determine the risk of oral cancer for the specimen provider according to the change of the RU value. In addition, it was known from the results from the fourth group to the sixth group that when the chip was designed with the anti-protein E6 antibody, changes of HPV contents of the specimens could not be detected, the detected RU variation was similar to the second group, thereby easily resulting in misjudge of the assessment of the risk of developing the oral cancer. In contrast, the THLW antibody disclosed by the present application still has detection effect to the fine variation of virus content in the specimen, that is, the THLW antibody disclosed by the present application has higher sensitivity and specificity than the anti-E6 monoclonal antibody.

Also, it can be known from the above results that when the detected RU variation is lower than 40, the risk for the specimen provider to develop the oral cancer is low; while when the detected RU variation is higher than 100, the risk for the specimen provider to develop the oral cancer is high, thereby presenting high risk of developing the oral cancer.

It can also be known from the above examples that THLW peptide represented by the SEQ ID No. 1 disclosed by the present application can be used as a biomarker for diseases relating to infection of HPV, further, THLW peptide and anti-THLW peptide antibody can be used as a tool of detecting the risk of developing the oral cancer in vitro. Furthermore, by combining the THLW peptide or/and the anti-THLW peptide antibody disclosed by the present application with detection tools, such as the biosensors, biochips, etc., or with the ELISA, it can be fast and effectively to clinically detect the risk of oral cancer.

The invention claimed is:

1. A method of detecting risk of developing oral cancer, the method comprising the following steps:
   a) preparing an anti-THLW antibody, wherein an amino acid of a THLW peptide is represented by SEQ ID No. 1, wherein the anti-THLW antibody recognizes an epitope comprised in SEQ ID NO: 1; and
   b) allowing the antibody of step a) to react with a specimen; and indicating that the specimen contains human papilloma virus and the specimen provider has a high risk of developing the oral cancer when a variation of a response unit (RU) between the specimen and the antibody is higher than a first preset value, or indicating that the specimen provider has a low risk of developing the oral cancer when the variation of the response unit between the specimen and the antibody is higher than a second preset value,
   wherein the RU is equivalent to values obtained for measuring antigen-antibody interaction in immune assays,
   wherein the specimen is saliva.

2. The method of claim 1, wherein the antibody is bond to a biochip.

3. The method of claim 1, wherein the step b) uses enzyme-linked immunosorbent assay to analyze reaction between the antibody and the specimen.

4. The method of claim 1, wherein the first preset value is 100 RU, and the second preset value is 40 RU.

* * * * *

SEQUENCE LISTING

<160> NUMBER OF SEQ ID NOS: 1

<210> SEQ ID NO 1
<211> LENGTH: 18
<212> TYPE: PRT
<213> ORGANISM: Artificial Sequence
<220> FEATURE:
<223> OTHER INFORMATION: artificial designed

<400> SEQUENCE: 1

```
Val Tyr Asp Phe Ala Phe Arg Asp Leu Cys Ile Val Tyr Arg Asp Gly
1               5                   10                  15

Asn Pro
```